United States Patent
Konate et al.

(10) Patent No.: US 9,226,882 B2
(45) Date of Patent: Jan. 5, 2016

(54) ECO-FRIENDLY NON-AQUEOUS ANTIMICROBIAL COMPOSITION COMPRISING TROPOLONE WITH 1,3-PROPANEDIOL AND/OR SORBITAN CAPRYLATE

(71) Applicant: ISP INVESTMENTS INC., Wilmington, DE (US)

(72) Inventors: Nadia Konate, Magdeburg (DE); Andrea Wingenfeld, Lauben (DE)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 14/420,051

(22) PCT Filed: Mar. 21, 2013

(86) PCT No.: PCT/US2013/033267
§ 371 (c)(1),
(2) Date: Feb. 6, 2015

(87) PCT Pub. No.: WO2014/025412
PCT Pub. Date: Feb. 13, 2014

(65) Prior Publication Data
US 2015/0216773 A1 Aug. 6, 2015

Related U.S. Application Data

(60) Provisional application No. 61/680,021, filed on Aug. 6, 2012.

(51) Int. Cl.
| | |
|---|---|
| *A61K 8/35* | (2006.01) |
| *A61Q 17/00* | (2006.01) |
| *A61Q 5/00* | (2006.01) |
| *A61K 8/34* | (2006.01) |
| *A61K 8/49* | (2006.01) |
| *A61Q 19/00* | (2006.01) |

(52) U.S. Cl.
CPC . *A61K 8/35* (2013.01); *A61K 8/345* (2013.01); *A61K 8/4973* (2013.01); *A61Q 5/00* (2013.01); *A61Q 17/005* (2013.01); *A61Q 19/00* (2013.01); *A61K 2800/10* (2013.01); *A61K 2800/30* (2013.01)

(58) Field of Classification Search
USPC .......................................................... 514/675
See application file for complete search history.

(56) References Cited

U.S. PATENT DOCUMENTS

| | | |
|---|---|---|
| 2002/0035160 A1 | 3/2002 | Nomura et al. |
| 2003/0039580 A1 | 2/2003 | Borokhov et al. |
| 2006/0233886 A1 | 10/2006 | Kielbania, Jr. et al. |
| 2007/0059331 A1 | 3/2007 | Schmaus et al. |
| 2012/0071390 A1 | 3/2012 | Fenyvesi et al. |
| 2012/0101135 A1 | 4/2012 | Klug et al. |

OTHER PUBLICATIONS

International Search Report, PCT/US2013/033267 published on Jun. 13, 2013.

*Primary Examiner* — Kristin Vajda
(74) *Attorney, Agent, or Firm* — William J. Davis

(57) ABSTRACT

Disclosed herein is an eco-friendly, non-aqueous and stable antimicrobial solution composition comprising (a) about 0.1 to 20.0 wt % of a Tropolone; and (b) about 80.0 to 99.9 wt % of bio-derived 1,3-propanediol and/or bio-derived sorbitan caprylate. Also disclosed is a process for preparing and method of using the composition. The composition is stable for at least two years at room temperature and can be employed in the fields of cosmetic, toiletry, personal care, household, cleaning, disinfecting, food, beverages, enzyme formulations, feminine care products, foot care products, pet care products, food ingredients, paints, coatings, metal working fluids, nutrients for plants, construction and/or laundry products.

18 Claims, No Drawings

ECO-FRIENDLY NON-AQUEOUS ANTIMICROBIAL COMPOSITION COMPRISING TROPOLONE WITH 1,3-PROPANEDIOL AND/OR SORBITAN CAPRYLATE

FIELD OF THE INVENTION

The present application relates to an antimicrobial composition, and more particularly, to an eco-friendly antimicrobial composition comprising tropolone and a solvent selected from 1,3-propanediol and/or sorbitan caprylate.

BACKGROUND OF THE INVENTION

Preservatives are employed in various non-limiting industrial applications including personal care, household, coatings, metalworking fluids, paper, wood, plastics, disinfection, cosmetics, toiletry, pharmaceuticals, food, beverages, oral care, paints, and water treatment to prevent microbial contamination, of which, the personal care products engage significant amount of preservatives. It is mandatory on the part of formulators to give due consideration for product safety and environmental impact of the ingredients of the composition that they develop.

The prior art discloses use of a variety of glycols for preparing preservative or antimicrobial compositions. Sometimes glycols per se are used as a preservative component. In many laboratories ethylene glycol has replaced formaldehyde to preserve organisms. However, the use of ethylene glycol is limited in food and personal care industries due its toxicity. So, there is a necessity to replace ethylene glycol with a solvent which is non toxic. The limitation of ethyleneglycol is partly addressed by chemically synthesized propylene glycol which has been widely used in many applications such as food, cosmetics, personal care, bakery, etc. Such compositions comprising chemically synthesized propylene diols were found to have an irritation potential, and harmful and toxic impurities produced from the chemical processes used to synthesize it.

Further, the use of diols, glycols and alcohols for preserving cosmetic, dermatological or pharmaceutical, personal care, household, disinfection, toiletry, food, beverage, and oral care compositions is limited by statutory regulatory instruments. Countries often have maximum concentration ranges to be employed in their respective approved regulated products. Additionally, an unwanted lowering of viscosity is observed with usage of higher percentage of solvents like alcohols in the end-user applications, thus, there is a limitation to employ higher concentration levels of alcohols.

To protect end-users against the microbial attack and from the side effects of excessive use levels of antimicrobial active ingredients, it is beneficial to have reduced concentration levels of Tropolone, an antimicrobial active of the present application. In this regard, mild and harmless efficacy enhancers of Tropolone could render the opportunity of decreasing the use concentration levels of Tropolone, an antimicrobial agent.

US Publication No. 20110086918 discloses a composition having effective broad spectrum preservation activity comprising benzyl alcohol, salicylic acid, sorbic acid, and a compound selected from the group consisting of 1,3-propanediol, glycerin and combinations thereof.

US Publication No. 20080176957 discloses a preservative compositions comprising 1,3-propanediol, wherein the 1,3-propanediol in said composition has a bio-based carbon content of about 1% to 100%. In addition, it is preferred that the 1,3-propanediol be biologically-derived, and wherein upon biodegradation, the biologically-derived 1,3-propanediol contributes no anthropogenic $CO_2$ emissions to the atmosphere.

US Publication No. 20120100085 discloses liquid compositions which contain (a) from 5 to 95% by wt of sorbitan monocaprylate and (b) from 5 to 95% by weight of one or more alcohols of formula (1) R—OH, and wherein the liquid compositions are suitable for the production of cosmetic, dermatological or pharmaceutical products.

US Publication No. 20090306154 discloses an antimicrobial mixture comprising or consisting of: (a) one, two or more tropolone derivatives; (b) one or more compounds selected from the group consisting of: chlorphenesin, imidazolidinyl urea, DMDM hydantoin, ethylhexylglycerin, diazolidinyl urea, sodium hydroxymethylglycinate and polyaminopropyl biguanide or salts or solvates thereof; and (c) one or more additional constituents selected from the group consisting of: methylchloroisothiazolinone, methylisothiazolinone, chlorohexidine, benzethonium chloride, 2-bromo-2-nitropropane-1,3-diol, methylpropanediol, dimethyl phenylpropanol and 4-methyl-4-phenyl-2-pentanol or salts or solvates thereof.

US Publication No. 20070265352 discloses an antimicrobial composition, comprising an antimicrobial effective amount of (a) at least one straight-chain 1,2-alkanediol, the chain length of which is in the range of 5 to 10 C-atoms, and (b) at least one preservative selected from sorbate and its salts, parabenes, iodopropynyl butylcarbamate, ethylene diamene tetraacetic acid and its salts, tropolone compounds and sisquiterpenes. Component (a) comprises: 1,2-hexanediol and 1,2-octanediol, 1,2-hexanediol and 1,2-decanediol, 1,2-pentanediol, 1,2-hexanediol and 1,2-octanediol, 1,2-hexanediol, 1,2-octanediol and 1,2-decanediol or 1,2-pentanediol, 1,2-hexanediol and 1,2-decanediol, the proportions of the said diols in the mixture being set such that their antimicrobial action is synergistically intensified.

US Publication No. 20070059331 discloses an antimicrobial mixtures comprising or consisting of one or more branched or unbranched alkanediols having 6-12 carbon atoms, one, two or more compounds chosen from the group consisting of the tropolones, wherein 1,2-hexanediol, 1,2-octanediol or 1,2-decanediol or a mixture of 1,2-hexanediol and 1,2-octanediol or a mixture of 1,2-hexanediol and 1,2-decanediol or a mixture of 1,2-octanediol and 1,2-decanediol or a mixture of 1,2-hexanediol, 1,2-octanediol and 1,2-decanediol is employed as constituent branched or unbranched alkanediols.

US Publication No. 20070054967 discloses antimicrobial active compounds, and in particular certain mixtures, formulations and foodstuffs comprising certain compounds (alcohols, ethers, esters, acids, corresponding salts and solvates) of a formula (I) and at least one tropolone (derivative) of the formula (II) and to products comprising such mixtures in an antimicrobially active amount.

US Publication No. 20120101135 discloses liquid compositions which contain (a) from 40 to 99.9% by wt of sorbitan monocaprylate and (b) from 0.1 to 60% by wt of one or more antimicrobial substances selected from the group consisting of the components (b1) to (b5): (b1) specific organic acids and the salts thereof, (b2) specific formaldehyde donors, (b3) specific isothiazolinones, (b4) specific paraben esters and the salts thereof, and (b5) specific pyridones and the salts thereof. The liquid compositions are suitable for the production of cosmetic, dermatological or pharmaceutical products.

The antimicrobial activity of tropolone and tropolone derivatives are known from the prior art, e.g., *Antimicrob.*

*Agents Chemother.* vol. 7(5), 500-506 (1975). However, the studies of synergistically intensified activity against antibacterial and antifungal strains of a combination of (i) Tropolone with (a) 1,3-propanediol and/or (b) sorbitan caprylate, bio-derived solvents is not disclosed in any prior art.

In view of foregoing, there remains a need for an eco-friendly, non-aqueous and stable antimicrobial solution composition comprising a solvent which is free from toxins, non-irritant for the skin, and preferably acceptable by various regulatory authorities around the globe.

Accordingly, it is a primary objective of the present application to provide an antimicrobial composition which can provide effective antimicrobial activity at lower use levels of the antimicrobial agent in the presence of said solvent or solvent system, i.e., 1,3-propanediol and/or sorbitan caprylate.

Another objective of the present application is to provide an antimicrobial composition comprising lower concentration levels of solvents such as alcohols in order to limit the impact on the viscosity of the end user products.

It is a further objective of the present application to provide an eco-friendly, non-aqueous and stable antimicrobial solution composition comprising (i) tropolone; (ii) 1,3-propanediol; and/or (iii) sorbitan caprylate.

SUMMARY OF THE INVENTION

The present application relates to an eco-friendly, non-aqueous and stable antimicrobial solution composition comprising (i) about 0.1 wt % to about 20 wt % of a Tropolone; and (ii) about 80.0 wt % to about 99.9 wt % of 1,3-propanediol, a bio-derived solvent and/or sorbitan caprylate, a bio-derived solvent.

In accordance with certain aspects, an eco-friendly non-aqueous antimicrobial composition is provided that is capable of withstanding heat and cold exposure, wherein the composition is stable for at least two years at room temperature or stable for at least 5 freeze/thaw cycles when the temperature is cycled from 50° C. to −24° C. in every 24 hours or stable for at least 4 weeks at about 50° C.

In accordance with another aspect of the present application, the eco-friendly, non-aqueous antimicrobial composition is capable of inhibiting or killing gram (+) bacteria, gram (−) bacteria, yeasts and/or fungi. The microorganisms of the present application are selected from the group including but are not limited to *Pseudomonas aeruginosa, Proteus mirabilis, Escherichia coli, Staphylococcus aureus, Burkholderia cepacia, Aspergillus brasiliensis, Penicillium expansum, Trichoderma viride* and/or *Candida albicans*.

In yet another aspect, the eco-friendly, non-aqueous antimicrobial composition of the present application is capable of demonstrating effective synergistic antimicrobial activity against bacteria, fungi and yeast in the presence of 1,3-propanediol, sorbitan caprylate alone or in combination.

In yet another aspect, the eco-friendly, non-aqueous antimicrobial composition of the present application is employed in the field of cosmetic, toiletry, personal care, household, cleaning, disinfecting, food, beverages, enzyme formulations, feminine care products, foot care products, pet care products, food ingredients, paints, coatings, metal working fluids, nutrients for plants and/or laundry products.

In accordance with another aspect of the present application, a process for preparing an eco-friendly, non-aqueous and stable antimicrobial solution composition comprises preparing a mixture of (a) about 0.1 wt % to about 20 wt % of a Tropolone; and (b) about 80 wt % to about 99.9 wt % of 1,3-propanediol a bio-derived solvent and/or sorbitan caprylate, a bio-derived solvent to yield a homogenous non-aqueous antimicrobial solution.

DETAILED DESCRIPTION OF THE INVENTION

While this specification concludes with claims particularly pointing out and distinctly claiming that which is regarded as the invention, it is anticipated that the invention can be more readily understood through reading the following detailed description of the invention and study of the included examples.

The singular forms "a," "an," and "the" include plural forms unless the context clearly dictates otherwise specified or clearly implied to the contrary by the context in which the reference is made. By the term "comprising" herein is meant that various optional, compatible components can be used in the compositions herein, provided that the important ingredients are present in the suitable form and concentrations. The term "comprising" thus encompasses and includes the more restrictive terms "consisting of" and "consisting essentially of" which can be used to characterize the essential ingredients such as Tropolone, 1,3-propanediol and/or sorbitan caprylate of the composition.

All percentages, parts, proportions and ratios as used herein, are by weight of the total composition, unless otherwise specified. All such weights as they pertain to listed ingredients are based on the raw material level.

All references to singular characteristics or limitations of the present invention shall include the corresponding plural characteristic or limitation, and vice-versa, unless otherwise specified or clearly implied to the contrary by the context in which the reference is made.

The term "about" can indicate a difference of 10 percent of the value specified. Numerical ranges as used herein are meant to include every number and subset of numbers enclosed within that range, whether particularly disclosed or not. Further, these numerical ranges should be construed as providing support for a claim directed to any number or subset of numbers in that range.

As used herein, the words "preferred," "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

References herein to "one embodiment", "one aspect" or "one version" or "one objective" of the invention include one or more such embodiment, aspect, version or objective, unless the context clearly dictates otherwise.

All publications, articles, papers, patents, patent publications, and other references cited herein are hereby incorporated herein in their entireties for all purposes to the extent consistent with the disclosure herein.

As used, herein, "stable" and "stability" mean a composition which is significantly unaffected in chemical nature, physical homogeneity and/or color upon exposure to conditions reasonably expected to be incurred in transport, storage and use. Stability may be determined either by empirical observation or by suitable methods of chemical and/or physical examination that would be known to one skilled in the art.

The term "eco-friendly" as used herein refers to antimicrobial composition comprising naturally-derived or nature-identical non toxic biodegradable ingredients. Further, the term "environmentally friendly" also means, without limitation, no adverse affect on the environment. More particularly, environmentally friendly, (also known as eco-friendly, nature friendly, and green) used to refer to goods and services, laws, guidelines and policies considered to inflict minimal or no harm on the environment or may rebuild or renew resources through their use.

The term "bio-derived" means produced or generated from a living organism such as one or more strains of bacteria, fungi, yeast and other microbial strains or from a plant or part of a plant through enzymatic reactions and/or simple chemical processes as they occur in nature.

The term "nature-identical compound" means a compound which has a chemical structure identical to that found in nature. The "nature-identical compound" includes synthetic compounds having the same chemical structure, regioisomeric form and stereo isomeric form as compounds produced by either a plant or animal origin.

As used herein, in reference to the compositions of the present application, the term "non-aqueous" means significantly free of water. Water is not purposely added to the compositions of the present application, and no effort has been made to exclude or remove small amount of water from the ingredients used in the compositions.

The term "sorbitan caprylate" and "sorbitan monocaprylate" is synonymously used in this specification and both the terms would refer the same compound.

What is described herein is an eco-friendly, non-aqueous and stable antimicrobial solution composition comprising (i) about 0.1 wt % to about 20.0 wt % of a Tropolone; and (ii) about 80.0 wt % to about 99.9 wt % of (a) 1,3-propanediol, a bio-derived solvent and/or (b) sorbitan caprylate, a bio-derived solvent.

The Tropolone (2-Hydroxy-2,4,6-cycloheptatrien-1-one) is an aromatic seven member ring compound with hydroxyl group in the 2-position to its ketone functional group. Tropolone is a metabolite of *Pseudomonas* sp. and its derivatives were isolated from fungi and higher plants. These tropolone compounds possess multiple biological activities such as antiviral, antimicrobial, and cytotoxic effects on various human cell lines. The tropolone, an antimicrobial agent of the present application can be isolated from plants that are known in the literature for a person skilled in the art. However, the non-limiting natural sources for isolating tropolone would include but are not limited to Cupressaceae family for example, *Chamaecyparis Lawsonia, Chamaecyparis Taiwanensis, Chamaecyparis Nootkatensis, Chamaecyparis Obtusa, Chamaecyparis Formosensis, Chamaecyparis Pisifera; Cupressus sempervirens; Thuja occidentalis, Thuja plicata; Thuyopsis Dolabrata*. The tropolone compound can be synthesized (Doering et al., J. Am. Chem. Soc. (1951), 73: 828-838) according to the prior art and employed for the purposes of the present application. Such laboratory synthesized nature identical compound can be purchased from commercial sources as well.

(a)

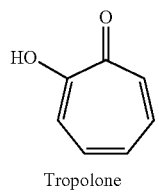

Tropolone

Tropolone is employed in the range of from about 0.1 wt % to 20.0 wt %. Other preferred ranges of Tropolone would include, but are not limited to, 0.1 wt % to 0.5 wt %, 0.5 wt % to 1.0 wt %, 1.5 wt % to 2.0 wt %, 2.0 wt % to 2.5 wt %, 2.5 wt % to 3.0 wt %, 3.0 wt % to 3.5 wt %, 3.5 wt % to 4.0 wt %, 4.0 wt % to 4.5 wt % or 4.5 wt % to 5.0 wt %, 5.0 wt % to 5.5 wt %, 5.5 wt % to 6.0 wt %, 6.0 wt % to 6.5 wt %, 6.5 wt % to 7.0 wt %, 7.0 wt % to 7.5 wt %, 7.5 wt % to 8.0 wt %, 8.0 wt % to 8.5 wt %, 8.5 wt % to 9.0 wt %, 9.0 wt % to 9.5 wt %, 9.5 wt % to 10.0 wt %, 10 wt % to 11 wt %, 11 wt % to 12 wt %, 12 wt % to 13 wt %, 13 wt % to 14 wt %, 14 wt % to 15 wt %, 15 wt % to 16 wt %, 16 wt % to 17 wt %, 17 wt % to 18 wt %, 18 wt % to 19 wt %, 19 wt % to 20 wt %.

The 1,3-propane-diol (b) (i), an eco-friendly, naturally occurring bio-derived solvent for dissolving the Tropolone of the present application is in the range of from about 80 wt % to 99.9 wt %. Other suitable or preferred ranges of 1,3-propane-diol would include, but are not limited to, 99 wt % to 98 wt %, 98 wt % to 97 wt %, 97 wt % to 96 wt %, 96 wt % to 95 wt %, 95 wt % to 94 wt %, 94 wt % to 93 wt %, 93 wt % to 92 wt %, 92 wt % to 91 wt %, 91 wt % to 90 wt %, 90 wt % to 89 wt %, 89 wt % to 88 wt %, 88 wt % to 87 wt %, 87 wt % to 86 wt %, 86 wt % to 85 wt %, 85 wt %, to 84 wt %, 84 wt % to 83 wt %, 83 wt % to 82 wt %, 82 wt % to 81 wt %, 81 wt % to 80 wt %. The 1,3-propane-diol is prepared or manufactured according to procedures known in the prior art. For example, the 1,3-propane-diol can be prepared in accordance with procedures and methods of US20070275139 assigned to Mellissa Joerger. For the purposes of the present invention, commercially available bio-derived 1,3-propanediol for example Zemea®, can be employed.

(b) (i)

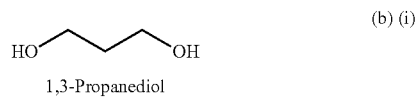

1,3-Propanediol

The sorbitan caprylate (b) (ii), is derived from renewable resources. It is eco-friendly, Ecocert-approved, non-listed preservative and can be used globally without regulatory limitations. Further, it has demonstrated literature on its boosting efficacy of classical preservatives such as organic acids and aromatic alcohols. It is low odor, non-volatile liquid and does not add odor even at high concentration of use levels.

(b) (ii)

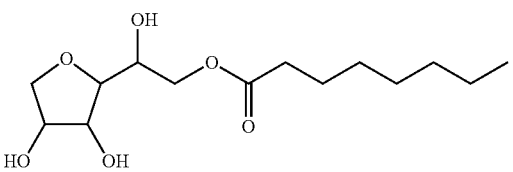

Sorbitan caprylate

The sorbitan caprylate for dissolving the Tropolone of the present application is in the range of from about 80 wt % to 99.9 wt %. Other suitable or preferred ranges of sorbitan caprylate would include but are not limited to 99 wt % to 98 wt %, 98 wt % to 97 wt %, 97 wt % to 96 wt %, 96 wt % to 95 wt %, 95 wt % to 94 wt %, 94 wt % to 93 wt %, 93 wt % to 92 wt %, 92 wt % to 91 wt %, 91 wt % to 90 wt %, 90 wt % to 89 wt %, 89 wt % to 88 wt %, 88 wt % to 87 wt %, 87 wt % to 86 wt %, 86 wt % to 85 wt %, 85 wt %, to 84 wt %, 84 wt % to 83 wt %, 83 wt % to 82 wt %, 82 wt % to 81 wt %, 81 wt % to 80 wt %. The sorbitan caprylate is derived or manufactured according to the procedures known in the prior art for a person skilled in the art. For the purposes of the present invention the commercially available bio-derived sorbitan caprylate, for example Velsan® SC, can be employed.

According to one important embodiment of the invention, the eco-friendly, non-aqueous and stable antimicrobial solution composition comprises (i) about 0.1 wt % to about 20.0 wt % of a Tropolone; and (ii) about 80.0 wt % to about 99.9 wt % of 1,3-propanediol and sorbitan caprylate, bio-derived solvents, wherein said 1,3-propanediol and sorbitan caprylate is in the ratio of 1:10 to 10:1. However the preferred ratio of the present application would include but are not limited to 1:1, 1:2, 2:1, 1:3, 3:1, 1:4, 4:1, 1:5, 5:1, 1:6, 6:1, 1:7, 7:1, 1:8, 8:1, 1:9 or 9:1. Most preferred ratio is 1:1, 1:3 or 3:1.

According to one alternative embodiment of the present application, it is contemplated to employ other biodegradable and eco-friendly glycol based compounds as a suitable solvent for the present application comprising propylene glycol, 1,3-butylene glycol, and 2-methyl-1,3-propanediol.

As per an optional embodiment of the present application, it is contemplated to employ other sorbitan ester derivatives, such as sorbitan cocoate, diisostearate, dioleate, distearate, isostearate, laurate, oleate, olivate, palmitate, sesquiisostearate, sesquioleate, sesquistearate, stearate, triisostearate, trioleate and the like.

According to one optional embodiment of the present application, one or more antimicrobial agents is additionally employed in the said antimicrobial preservative composition, preferably in the concentration of 1% to 10% of the total composition. The preferred antimicrobial agents of the present application are selected from the group including, but not limited to, benzoic acid and sodium salt, propionic acid and its salts, salicylic acid and its salts, sorbic acid and its salts, formaldehyde, paraformaldehyde, biphenyl-2-ol (o-phenylphenol) and its salts, zinc pyrithione, chlorobutanol, 4-hydroxybenzoic acid its salts and esters, dehydroacetic acid and its salts, formic acid and its sodium salt, 3,3'-dibromo-4,4'-hexamethylene-dioxydibenzamidine, 3,3'-dibromo-4,4'-hexamethylenedioxydibenzamidine isethionate salt, thiomersal, phenylmercuric salts, undec-10-enoic acid and salts, hexetidine, 5-bromo-5-nitro-1,3 dioxane, bronopol, 2,4-dichlorobenzyl alcohol, triclocarban, 4-chloro-m-cresol, triclosan, 4-chloro-3,5-xylenol, 3,3'-bis-(1-hydroxymethyl-2,5-dioxoimidazolidin-4-yl)-1,1'-methylenediurea, poly(1-hexamethylenebiguanide hydrochloride), 2-phenoxyethanol, hexamethylenetetramine, methenamine-3-chloroallylochloride, 1-(4-Chlorophenoxy)-1-(imidazol-1-yl)-3,3-dimethylbutan-2-one, 1,3-bis(hydroxymethyl)-5,5-dimethylimidazolidine-2,4-dione, benzyl alcohol, 1-hydroxy-4-methyl-6(2,4,4-trimethylpentyl)-2-pyridon and monoethanolamine salt, 6,6-dibromo-4,4-dichloro-2,2'-methylenediphenol, 4-isopropyl-m-cresol, mixture of 5-chloro-2-methyl-isothiazol-3(2H)-one (CMIT) and 2-methylisothiazol-3(2H)-one (MIT) with magnesium chloride and magnesium nitrate, 2-benzyl-4-chlorophenol (chlorophene), 2-chloroacetamide, chlorhexidine digluconate, chlorhexidine diacetate, chlorhexidine dihydrochloride, 1-phenoxypropan-2-ol, alkyl ($C_{12}$-$C_{22}$) trimethyl ammonium, bromide and chloride, 4,4-dimethyl-1,3-oxazolidine, N-(hydroxymethyl)-N-(dihydroxymethyl-1,3-dioxo-2,5-imidazolinidyl-4)-N'-(hydroxymethyl) urea, hexamidine isethionate, hexamidine p-hydroxy-benzoate, glutaraldehyde (Pentane-1,5-dial), 5-ethyl-3,7-dioxa-1-azabicyclo[3.3.0]octane, 3-(p-chlorophenoxy)-propane-1,2-diol (chlorphenesin), sodium hydroxymethylamino acetate (sodium hydroxymethylglycinate), silver chloride deposited on titanium dioxide, benzethonium chloride, benzalkonium chloride, bromide and saccharinate, iodopropynyl butyl-carbamate (IPBC), diazolidinyl urea, imidazolidinyl urea, bromonitropropanediol and combinations thereof.

According to important embodiment of the invention, at least one UV-filter compound can be added to the eco-friendly, non-aqueous and stable antimicrobial solution composition of the present application. Such UV filter compounds can be selected from organic or inorganic compounds. The non-limiting organic UV filter compounds are selected from the group consisting of 2-ethylhexyl 2-cyano-3,3-diphenylacrylate (octocrylene), ethyl 2-cyano-3,3-diphenylacrylate; 4-methyl benzylidene camphor, 3-benzylidene camphor, camphor benzalkonium methosulfate, polyacrylamidomethyl benzylidene camphor, sulfo benzylidene camphor, sulphomethyl benzylidene camphor, terephthalylidene dicamphor sulfonic acid; ethylhexyl methoxycinnamate, ethoxyethyl methoxycinnamate, isoamyl methoxycinnamate, cinnamic acid derivatives bond to siloxanes; p-aminobenzoic acid derivatives including p-aminobenzoic acid, 2-ethylhexyl p-dimethylaminobenzoate, N-oxypropylenated ethyl p-aminobenzoate, glyceryl p-aminobenzoate; benzophenones e.g. benzophenone-3, benzophenone-4,2,2',4,4'-tetrahydroxy-benzophenone, 2,2'-dihydroxy-4,4'-dimethoxybenzophenone; di-(2ethylhexyl)-4-methoxybenzalmalonate; organosiloxane compounds with chromophore groups like polysilicones-15, drometrizole trisiloxane; isopropylbenzyl salicylate, benzyl salicylate, butyl salicylate, ethylhexyl salicylate, isooctyl salicylate or homomethyl salicylate; ethylhexyl triazone, diethylhexyl butamido triazone, bis-ethylhexyloxyphenol methoxyphenyl triazine (Tinosorb® 5); 2,2'-methylene-bis-(6(2H-benzotriazole-2-yl)-4-(1,1,3,3,-tetramethylbutyl)-phenol (Tinosorb® 5); encapsulated ethylhexyl methoxycinnamate or microcapsules loaded with UV-filters as revealed in EP1471995; 4-tert-butyl-4'-methoxydibenzoyl-methane, dimethoxydibenzoyl-methane, isopropyldibenzoylmethane; 2,2-(1,4-phenylene) bis-(1H-benzimidazo[4,6-d]sulfonic acid) (Neoheliopan AP); 2-(4-diethylamino-2-hydroxybenzoyl)-benzoic acid hexylester; 2,4-bis-[5-1(dimethylpropyl)benzoxazol-2-yl-(4-phenyl)imino]-6-(2-ethylhexyl)-imino-1,3,5-triazine.

The preferred list of UV filters for the present application is selected from the group including but not limited to 1-(4-Tert-butylphenyl)-3-(4-methoxyphenyl)propane-1,3-dione; α-(2-oxoborn-3-ylidene) toluene-4-sulphonic acid and its salts; 2-cyano-3,3-diphenylacrylic acid, octocrylene; polymer of N-{(2 and 4)[(2-oxoborn-3-ylidene)methyl] benzyl}acrylamide; octyl methoxycinnamate; ethoxylated-ethyl-1-aminobenzoate; isoamyl-p-methoxycinnamate; 2,4,6-Trianilino-(p-carbo-2'-ethylhexyl-1'-oxy)-1,3,5-triazine (Octyl triazone); phenol-2-2(2H-benzotriazol-2-yl)-4-methyl-6-(2-methyl-3-(1,3,3,3-tetramethyl-1-(trimethylsilyl) oxy)-disiloxanyl)-propyl (Drometriazole Trisiloxane); benzoic acid, 4,4-((6-(((1,1-dimethylethyl)amino)carbonyl)phenyl)amino)-1,3,5-triazine-2,4-diyl)diimino)bis-,bis(2-ethylhexyl)ester); 4-methylbenzylidene camphor; 3-Benzylidene camphor; octyl salicylate; 4-dimethyl-aminobenzoate of ethyl-2-hexyl (octyl dimethyl PABA); 2-hydroxy-4-methoxybenzo-phenone-5-sulfonic acid and its sodium salt; 2,2'-Methylene-bis-6-(2H-benzotriazol-2yl)-4-(tetramethyl-butyl)-1,1,3,3-phenol; Monosodium of 2-2'-bis-(1,4-phenylene) 1Hbenzimidazole-4,6-disulphonic acid; (1,3,5)-Triazine-2,4-bis((4-(2-ethyl-hexyloxy)-2-hydroxy)-phenyl)-6-(4-methoxyphenyl).

Accordingly, the preferred inorganic UV filter compounds would include microparticulated Zinc oxide or Titanium dioxide and other known inorganic compounds that are readily available for a person skilled in the art.

In a preferred embodiment of this application, the eco-friendly, non-aqueous and stable antimicrobial solution composition further comprises sequestering or chelating agent in order to stabilize tropolone, an antimicrobial agent and wherein said sequestering or chelating is selected from the group comprising polyols, gluconates, sorbitals, mannitols, carbonates, hydroxamates, catechols, α-amino carboxylates, alkanolamines, metal-ion sequestrants, hydroxy-carboxylic acids, aminocarboxylic acids, amino polycarboxylic acids, polyamines, polyphosphates, phosphonic acids, crown ethers, amino acids, polycarboxylic acids, cyclodextrin, phosphonates, polyacrylates or polymeric polycarboxylates, condensed phosphates, However, the particular sequestering or chelating agents of the present invention would include but are not limited to acetic acid, adenine, adipic acid, ADP, alanine, alanine, albumin, arginine, ascorbic acid, asparagine, aspartic acid, ATP, benzoic acid, n-butyric acid, casein, citraconic acid, citric acid, cysteine, dehydracetic acid, desferri-ferrichrysin, desferri-ferrichrome, desferri-ferrioxamin E, 3,4-dihydroxybenzoic acid, diethylenetriaminepentaacetic acid (DTPA), hydroxylpropylenediaminetetraacetic acid (DPTA), dimethylglyoxime, dimethylpurpurogallin, EDTA, formic acid, fumaric acid, globulin, gluconic acid and its alkali metal salts, glutamic acid, Tetra sodium glutamate diacetate, Tetrasodium Iminodisuccinate, glutaric acid, glycine, glycolic acid, glycylglycine, glycylsarcosine, guanosine, histamine, salicylic, pimalic and sulfamic acid, salicylic, glutaric, malonic acid, 1,10-phenanthroline, 2-pyridylacetic acid, 5-formylfuran sulfonic acid, N-tris(hydroxymethyl)methyl-2-aminoethanesulfonic acid, itaconic acid, chelidonic acid, 3-methyl-1,2-cyclopentanedione, glycolamide, histidine, 3-hydroxyflavone, inosine, iron-free ferrichrome, isovaleric acid, itaconic acid, kojic acid, lactic acid, leucine, lysine, maleic acid, malic acid, methionine, methylsalicylate, nitrilotriacetic acid (NTA), nitrilotriacetic acid dodium salts (NTA slats), ornithine, orthophosphate, oxalic acid, oxystearin, phenylalanine, phosphoric acid, phytate, pimelic acid, pivalic acid, polyphosphate, proline, propionic acid, purine, pyrophosphate, pyruvic acid, riboflavin, salicylaldehyde, salicyclic acid, sarcosine, serine, sorbitol, succinic acid, tartaric acid, tetrametaphosphate, thiosulfate, threonine, trimetaphosphate, triphosphate, tryptophan, uridine diphosphate, uridine triphosphate, n-valeric acid, valine, xanthosine, triethylenetetraaminehexaacetic acid, N,N'-bis (o-hydroxybenzyl) ethylenediamine-N,N' diacteic acid, ethylenebis-N,N'-(2-o-hydroxyphenyl)glycine, acetohydroxamic acid, desferroxamine-B, disulfocatechol, dimethyl-2,3-dihydroxybenzamide, mesitylene catecholamide (MECAM), 1,8-dihydroxynaphthalene-3,6-sulfonic acid, and 2,3-dihydroxynaphthalene-6-sulfonic acid, siderophores molecules, N,N-dicarboxymethyl-2-aminopentanedioic-acid, diethylenetriaminepentaacetic-acid, ethylene-diaminetetraacetates e.g. Tetrasodium EDTA, nitriloacetates or N-(2-hydroxyethyl)nitrilodiacetates), Trisodium Ethylenediamine Disuccinate, 2,2-dichloropropionic acid, 2,2-dibromobutyric acid, trifluoroacetic acid, tribromoacetic acid, trichloroacetic acid, 2,3-dibromopropionic acid, 2,2-dichlorovaleric acid, 3-nitropropionic acid, triiodoacetic acid, 3(2,2,2-trichloroethoxy) propionic acid, 4-nitro-2-chlorobutyric acid, 2-bromo-2-nitropropionic acid, 2-nitroacetic acid, 2,4-dihydroxyphenyl acetic acid, 2,4-dichlorophenyl acetic acid, 3 (2',4'-dibromophenoxy)propionic acid, 3(3',5'-dinitrophenoxy)propionic acid, 3-phenyl-2,3-dibromopropionic acid, 3,5-dinitro-salicylic acid, 3(3'-bromo-4'-nitrophenyl)propionic acid, 3(3',4'-dihydroxyphenyl)propionic acid alone or in combination. Further information on sequestering and chelating agents is disclosed in T. E. Furia, CRC Handbook of Food Additives, $2^{nd}$ Edition, pp. 271-294 (1972), and M. S. Peterson and A. M. Johnson (Eds.), Encyclopedia of Food Science, pp. 694-699 (1978) are incorporated herein by reference in its entirety. The most preferred metal-ions used to chelate with tropolone compound are selected from the group consisting of copper, ferrous, ferric, zinc, magnesium, calcium and manganese.

Apart from chelation, tropolone compound can be complexed with preferred metal ions and used for the purposes of the present application as disclosed in U.S. Pat. No. 7,427,316 assigned to DuPont the disclosure of which is hereby incorporated herein in its entirety.

One important embodiment of the present application is to provide an antimicrobial solution composition with eco-friendly nature. The composition of the present application provides enhanced compatibility with all cosmetic, toiletry, personal care, household, cleaning, disinfecting, food, beverages, enzyme formulations, feminine care products, foot care products, pet care products, food ingredients, paints, coatings, metal working fluids, nutrients for plants and/or laundry products.

In accordance with another embodiment of the present application, the antimicrobial composition is capable of inhibiting or killing microorganisms, bacteria, yeasts and fungi, molds or spores that are selected from a group including, but are not limited to, *Candida tropicalis, Candida albicans, Hansenula anomala, Saccharomyces cerevisiae, Torulaspora delbreuckii, Zygosaccharomyces bailii, Zygosaccharomyces rouxii, Bacillus subtilis, Bacillus cereus, Staphylococcus aureus, Staphylococus epidermidis, Escherichia coli, Salmonella typhimurium, Salmonella enteritidis, Vibrio parahaemolyticus, Pseudomonas aeruginosa, Aspergillus niger, Aspergillus flavus, Penicillium islandicum, Penicillium citrinum, Penicillium chrysogenum, Fusarium oxysporum, Fusarium graminearum, Fusarium solani, Alternaria alternata*, and/or *Mucor racemosus, Penicillium funiculosum, Aureobasidium pullulans, Gliocladium riruns, Rhizopus javanicus, Penicillium notatum, Leuconostoc citreum*, and/or *Leuconostoc gelidium*. The preferred microorganisms of the present application is *Pseudomonas aeruginosa, Proteus mirabilis, Escherichia coli, Staphylococcus aureus, Burkholderia cepacia, Aspergillus brasiliensis, Penicillium expansum, Trichoderma viride* and/or *Candida albicans.*

Further, the use levels of Tropolone required for an adequate preservation of the desired products can be significantly decreased in combination with 1,3-propanediol and/or sorbitan caprylate by their unexpected synergism. In so doing, the use of Tropolone is often sufficient enough for the preservation of desired products.

The minimum inhibitory concentration (MIC) level of tropolone is reduced >50% in presence of 1,3-propanediol (Zemea) against *Escherichia coli*. The sorbitan caprylate (Velsan SC) is able to reduce the MIC level of tropolone by >90% against *Burkholderia cepacia*. Similarly, the sorbitan caprylate (Velsan SC) is able to reduce the MIC level of tropolone by >50% against *Aspergillus brasiliensis* and *Trichoderma viride*.

The following is a representative list of some of the numerous possible applications of the preservative antimicrobial composition. It should be understood that this list is presented for illustrative purposes only and does not represent any limitation as to possible applications.

(i) Cosmetic products: sunscreens; suntan lotions; after-sun gels, lotions and creams; antiperspirants; deodorants (solutions, powders, gels, roll-ons, sticks, sprays, pastes, creams, lotions); cleansing creams; skin conditioners; skin moisturizers; protectants; skin aging products; skin wrinkle reduction products; products for treatment of acne; products for treatment of rosacea; age-spot reduction products; stretch-mark reduction products; pimple treatment products, skin soothing products; skin infection and lesion treatment products; skin-redness reduction products; stretch-mark reduction products; varicose and spider-vein reduction products; lotions; oils; hand/body creams; shaving gels/creams; body washes; liquid and solid soaps; blood microcirculation improvement products, cellulite reduction products, body toning products, skin penetration enhancers; skin whitening products; cosmetics; shampoos; shower gels; bubble baths; hair treatment products, e.g., conditioning shampoos, medicated shampoos, mousses, waxes, conditioners, styling agents, lotions, pomades, spray gels, hair dyes and tints, colorant and non-colorant rinses, detangling lotions, hair curling and hair straightening products, hair wave products, hair styling gels, hair reparatives, hair tonics, hair fixatives, hair mousses, etc. hand (or mechanical) dishwashing compositions, hand sanitizers, disinfectants, lipsticks and lip balms, salves, collodion, impregnated patches and strips for skin treatment, skin surface implants, impregnated or coated diapers, moisturizing compositions, skin toners, skin cleansers, night creams, skin creams, shaving creams, skin care lotions, make-up, foundation, liquid, powder-based make-up, mascara, lipstick, blush, gloss, eye-liner, sunscreens, fragrances, massage oil, bath and shower gels, liquid soaps, moisturizing pressed powder formulations, bath additives, foaming soaps and body washes, sanitizing wipes, hand sanitizers, towelettes and wipes and the like. It should be understood, based on this brief disclosure that a wide range of cosmetic and toiletry formulations can be benefitted from the compositions of the present application.

(ii) Dental care: mouthwash; dentifrice; dental floss coated and/or impregnated with the composition; protective coating for teeth; toothbrush bristles coated and/or impregnated with the composition; orthodontic appliance coated and/or impregnated with the composition; orthodontic appliance adhesive; denture appliance coated and/or impregnated with the composition; denture appliance adhesive; endodontic composition coated and/or impregnated with the composition; composite-type dental restorative materials; dental cement; dental liner; dental bonding agent; and the like.

(iii) Foods and food products: food-stuffs; animal feed-stuffs; grains; breads; bakery products; confectionary; potato products; pasta products; salads; soups; seasonings; condiments; syrups; jams, jellies and marmalades; dairy products; egg-based products; meats and meat-based products; poultry and poultry-based products; fish and fish-based products; crustaceans and crustacean-based products; fresh and dried fruit products; vegetables and vegetable products; greens; salads; sauces; beverages, e.g., wines, tea extracts, beers, juices; and the like.

(iv) Plastics and miscellaneous products, coated and/or impregnated with the composition, including: medical items, e.g., thermometers, catheters, surgical sutures, blood lines, implants, bandages, surgical dressings, surgical apparel, respirators, etc.; food packaging; drug and cosmetic packaging; eating utensils; shower curtains; bath mats; sponges; mops; toilet seats, rubber gloves; contact lenses; hearing aids; shelving paper; carpet pads; pool covers; animal bedding and cat litter; computer covers and computer keys; doorknobs; tampons and sanitary napkins; dental chairs; dryer sheets; dishcloths; paints and coatings; powdered, liquid, gel and spray cleaners for floors sinks, counter-tops, walls, tiles, floors, carpets; deodorizing liquids, solids, sprays, gels and powders; filters; foams; hair brushes; combs; diaper rash preventer; plasma bag treatment; disposable glove treatment; additive to pasteurized cow milk; additive to blood sample tubes to inactivate HIV, HCMV, and other viruses (safety measure for lab technicians and healthcare providers); additives for condoms, band-aids, or bandages; additive for paint; or animal or plant treatment for microbial infections; and the like.

(v) Fibers and fabrics coated and/or impregnated with the composition, including natural and synthetic fibers and fabrics manufactured from such fibers; wipes, cloths; surgical gauze; crib covers; bassinet covers; bed linens; towels and wash cloths; tents; draw sheets; cubicle curtains; shower curtains; wall coverings; wood and wood products; hospital clothing such as examination robes, physicians' coats, nurses uniforms, etc.; apparel; paper, non-woven fabric, knitted fabric, woven fabric, brick, stone, plastic, polymer, latex, metal, tile, walls, floors, gurneys, tables, or trays; shoes and the like.

(vi) Industrial products: Agricultural sector, pesticide preparations, polymer dispersions, adhesives, thickeners, paints, coatings, metal working, pigment dispersions, photographic materials.

(vii) Cleaning and disinfecting: It is contemplated that the preservative composition of the present application is useful for cleaning, disinfecting or inhibiting microbial growth on any hard surface. Examples of surfaces, which may be contacted with the composition of the invention are surfaces of process equipment used e.g. dairies, chemical or pharmaceutical process plants, water sanitation systems, oil processing plants, paper pulp processing plants, water treatment plants, and cooling towers. Additionally, the preservative composition be used for cleaning surfaces and cooking utensils in food processing plants and in any area in which food is prepared or served such as hospitals, nursing homes, restaurants, especially fast food restaurants, delicatessens and the like. It may also be used as a preservation agent or a disinfection agent in water based paints, microbial control of water lines, and for disinfection of water, in particular for disinfection of industrial water.

Suitable application forms for delivering the present antimicrobial preservative composition include but are not limited to emulsion, lotion, milk, fluid, cream, alcoholic or aqueous/alcoholic solution, liquid soap, shampoo, stick or makeup, stick, roll-ons, spray, pump-spray, aerosol, soap bar, powder, solution, gel, cream, balm, towelettes and wipes and lotion. However the preferred form for delivering the present composition is a solution.

One important embodiment discloses a process for preparing an eco-friendly, non-aqueous and stable antimicrobial solution composition comprising: preparing a mixture of (a) about 0.1 to 20.0 wt % of a tropolone; and (b) about 80.0 to 99.9 wt % of 1,3-propanediol and/or sorbitan caprylate, bio-derived solvents at ambient/room temperature conditions to yield a homogenous non-aqueous antimicrobial solution.

In yet another embodiment, the present application provides an eco-friendly, non-aqueous and stable antimicrobial solution composition comprising: about 0.1 to 20.0 wt % of a Tropolone; and about 49.95 to 40.0 wt % of (i) 1,3-propanediol, a bio-derived solvent; and about 49.95 to 40.0 of (ii) sorbitan caprylate, a bio-derived solvent.

Another embodiment of the present application provides a method for inhibiting or killing microbial growth comprising mixing a effective amount of antimicrobial composition of the present invention with an appropriate product selected from the group consisting of cosmetic, toiletry, personal care, household, cleaning, disinfecting, food, beverages, enzyme formulations, feminine care products, foot care products, pet care products, food ingredients, paints, coatings, metal working fluids, nutrients for plants and/or laundry products; wherein, the effective amount of preservative composition is in the range of 0.01 wt % to about 25 wt % of the total composition. The other preferred effective amount of preservative composition ranges includes but not limited to 0.01 wt % to 5 wt %, 5 wt % to 10 wt %, 10 wt % to 15 wt %, 15 wt % to 20 wt % or 20 wt % to 25 wt %. The most preferred effective amount of preservative composition range is 0.01 wt % to 5 wt %.

Further, certain aspects of the present invention are illustrated in detail by way of the following examples. The examples are given herein for illustration of the invention and are not intended to be limiting thereof.

EXAMPLE 1

1% Tropolone and 99% 1,3-propanediol and sorbitan caprylate

The antimicrobial solution composition is prepared by mixing (a) about 1.0 wt % of a Tropolone; and (b) about 99 wt % of a 1,3-propanediol and sorbitan caprylate to yield a homogenous non-aqueous antimicrobial solution. The composition is stable for at least two years at room temperature or stable for at least 5 freeze/thaw cycles when the temperature is cycled from 50° C. to −24° C. in every 24 hours or stable for at least 4 weeks at about 50° C.

| Antimicrobial Composition | wt % |
|---|---|
| Tropolone | 1 |
| 1,3-Propane-diol and Sorbitan caprylate (1:1 ratio) | 99 |

EXAMPLE 2

1% Tropolone and 99% 1,3-propanediol or sorbitan caprylate

The antimicrobial solution composition is prepared by mixing (a) about 1.0 wt % of a Tropolone; and (b) about 99 wt % of a 1,3-propanediol or sorbitan caprylate to yield a homogenous non-aqueous antimicrobial solution. The composition is stable for at least two years at room temperature or stable for at least 5 freeze/thaw cycles when the temperature is cycled from 50° C. to −24° C. in every 24 hours or stable for at least 4 weeks at about 50° C.

| Antimicrobial Composition | wt % |
|---|---|
| Tropolone | 1 |
| 1,3-Propane-diol or Sorbitan caprylate | 99 |

EXAMPLE 3

2% Tropolone and 98% 1,3-propanediol and sorbitan caprylate

The antimicrobial solution composition is prepared by mixing (a) about 2.0 wt % of a Tropolone; and (b) about 98 wt % of a 1,3-propanediol and sorbitan caprylate to yield a homogenous non-aqueous antimicrobial solution. The composition is stable for at least two years at room temperature or stable for at least 5 freeze/thaw cycles when the temperature is cycled from 50° C. to −24° C. in every 24 hours or stable for at least 4 weeks at about 50° C.

| Antimicrobial Composition | wt % |
|---|---|
| Tropolone | 2 |
| 1,3-Propane-diol and Sorbitan caprylate (1:1 ratio) | 98 |

EXAMPLE 4

2% Tropolone and 98% 1,3-propanediol and sorbitan caprylate

The antimicrobial solution composition is prepared by mixing (a) about 2.0 wt % of a Tropolone; and (b) about 98 wt % of a 1,3-propanediol and sorbitan caprylate to yield a homogenous non-aqueous antimicrobial solution. The composition is stable for at least two years at room temperature or stable for at least 5 freeze/thaw cycles when the temperature is cycled from 50° C. to −24° C. in every 24 hours or stable for at least 4 weeks at about 50° C.

| Antimicrobial Composition | wt % |
|---|---|
| Tropolone | 2 |
| 1,3-Propane-diol and Sorbitan caprylate (1:3 ratio) | 98 |

EXAMPLE 5

2% Tropolone and 98% 1,3-propanediol and sorbitan caprylate

The antimicrobial solution composition is prepared by mixing (a) about 2.0 wt % of a Tropolone; and (b) about 98 wt % of a 1,3-propanediol and sorbitan caprylate to yield a homogenous non-aqueous antimicrobial solution. The composition is stable for at least two years at room temperature or stable for at least 5 freeze/thaw cycles when the temperature is cycled from 50° C. to −24° C. in every 24 hours or stable for at least 4 weeks at about 50° C.

| Antimicrobial Composition | wt % |
|---|---|
| Tropolone | 2 |
| 1,3-Propane-diol and Sorbitan caprylate (3:1 ratio) | 98 |

EXAMPLE 6

2% Tropolone and 98% 1,3-propanediol or sorbitan caprylate

The antimicrobial solution composition is prepared by mixing (a) about 2.0 wt % of a Tropolone; and (b) about 98 wt % of 1,3-propanediol or sorbitan caprylate to yield a homogenous non-aqueous antimicrobial solution. The composition is stable for at least two years at room temperature or stable for at least 5 freeze/thaw cycles when the temperature is cycled from 50° C. to −24° C. in every 24 hours or stable for at least 4 weeks at about 50° C.

| Antimicrobial Composition | wt % |
|---|---|
| Tropolone | 2 |
| 1,3-Propane-diol or Sorbitan caprylate | 98 |

EXAMPLE 7

3% Tropolone and 97% 1,3-propanediol and sorbitan caprylate

The antimicrobial solution composition is prepared by mixing (a) about 3.0 wt % of a Tropolone; and (b) about 97 wt % of a 1,3-propanediol and sorbitan caprylate to yield a homogenous non-aqueous antimicrobial solution. The composition is stable for at least two years at room temperature or stable for at least 5 freeze/thaw cycles when the temperature is cycled from 50° C. to −24° C. in every 24 hours or stable for at least 4 weeks at about 50° C.

| Antimicrobial Composition | wt % |
|---|---|
| Tropolone | 3 |
| 1,3-Propane-diol and Sorbitan caprylate (1:1 ratio) | 97 |

EXAMPLE 8

3% Tropolone and 97% 1,3-propanediol or sorbitan caprylate

The antimicrobial solution composition is prepared by mixing (a) about 3.0 wt % of a Tropolone; and (b) about 97 wt % of a 1,3-propanediol or sorbitan caprylate to yield a homogenous non-aqueous antimicrobial solution. The composition is stable for at least two years at room temperature or stable for at least 5 freeze/thaw cycles when the temperature is cycled from 50° C. to −24° C. in every 24 hours or stable for at least 4 weeks at about 50° C.

| Antimicrobial Composition | wt % |
|---|---|
| Tropolone | 3 |
| 1,3-Propane-diol or Sorbitan caprylate | 97 |

EXAMPLE 9

Antimicrobial Activity (MIC study) for (1) Tropolone and 1,3-Propanediol, (2) Tropolone and sorbitan caprylate The antimicrobial (bacterial, fungal, yeast) studies were conducted for compositions of example 6 at concentrations ranging from 20 ppm to 500 ppm to obtain the Minimum Inhibitory Concentration (MIC) of the said compositions for selected types of bacterial and fungal strains.

The individual concentrations of the test-product were weighed into sterile Erlenmeyer flasks and mixed with 100 ml of an appropriate growth media at a maximum temperature of about 40 to 50° C. Equal amounts of mixtures were poured into four Petri dishes. After cooling, the Petri dishes were inoculated with the respective standard strains. During the experiment, the Petri dishes were kept for 2 to 3 weeks at room temperature of about 20 to 25° C. in the dark. The following two different types of culture media were employed for the present studies:
  i. Bacteria-Agar: merchantable Caso-Agar pH-Value: 7.3±0.2
  ii. Fungi/Yeast-Agar: merchantable Malt extract-Agar (3%) pH-Value: 5.6±0.2

The preferred bacterial strains for the present application are *Pseudomonas aeruginosa* (DSM 1128), *Staphylococcus aureus* (DSM 799), *E. Coli* (DSM 1576), *Proteus mirabilis* (DSM 788) and *Burkholderia cepacia* (DSM 7288), and the preferred fungal strains are *Aspergillus brasiliensis* (DSM 1988), *Penicillium expansum* (DSM 1282), *Trichoderma viride* (DSM 63064), and the yeast is *Candida albicans*, (DSM 1386). After $2^{nd}$ and $3^{rd}$ weeks macroscopic evaluations were performed, the ratings are as follows:

Evaluation criteria for Bacteria and Yeast

+++ Strong growth
++ Growth
+ Slight growth
− No growth

Evaluation criteria for Fungi

+++ Petri dish completely overgrown
++ Petri dish 50% overgrown
+ Growth only at inoculation points
− No growth The formulation under examination is considered to be efficient if the following conditions are duly fulfilled i.e. (i) after 2-3 weeks no growth of the tested culture is visible; (ii) with rising concentration of the tested formulation, the germ growth should macroscopically be reduced until it is not visible any more. The obtained MIC levels are disclosed in Table 1, 2 and 3.

TABLE 1

MIC levels for bacterial strains of Example 6:

| | MIC (ppm) | | |
|---|---|---|---|
| Antimicrobial strain | Tropolone | Tropolone + 1,3-Propandiol | Tropolone + Sorbitan caprylate |
| *Pseudomonas aeruginosa* | 500 | 500 | 500 |
| *Proteus mirabilis* | 250 | 250 | 250 |
| *Escherichia coli* | 250 | 100 | 250 |
| *Staphylococcus aureus* | 250 | 250 | 250 |
| *Burkholderia cepacia* | 250 | 500 | 20 |

TABLE 2

MIC levels for fungal strains of Example 6:

| | MIC (ppm) | | |
|---|---|---|---|
| Antifungal strain | Tropolone | Tropolone + 1,3-Propandiol | Tropolone + Sorbitan caprylate |
| *Aspergillus brasiliensis* | 50 | 50 | 20 |
| *Trichoderma viride* | 250 | 250 | 100 |
| *Penicillim expansum* | 100 | 50 | 100 |

TABLE 3

MIC levels for yeast strains of Example 6:

| Yeast strain | MIC (ppm) | | |
| --- | --- | --- | --- |
| | Tropolone | Tropolone + 1,3-Propanediol | Tropolone + Sorbitan caprylate |
| Candida albican | 20 | 20 | 20 |

EXAMPLE 10

Antimicrobial Study of Example 6 in Hair Gel Product

The preserved and non-preserved (control) hair gel products were weakly inoculated 4 times with $10^5$ cfu/g and strongly inoculated once with $10^7$-$10^8$ cfu/g of a bacterial and a fungal composite. The microbes inoculated products were preserved with 0.8%, 1.3%, 2.0% and 3.0% of the total composition of example 6. The hair gel products were evaluated several times for microbial counts at various days intervals after the first, the third and the fifth inoculation. The hair gel products were free of microbes 1 day after the first (weak) inoculation and 2 days after the fifth inoculation (strong). The unpreserved hair gel product was still heavily contaminated at the end of the 10 weeks of observation.

EXAMPLE 11

Antimicrobial Study of Example 6 in Cream Product

The preserved and non-preserved (control) hair gel products were weakly inoculated 4 times with $10^5$ cfu/g and strongly inoculated once with $10^7$-$10^8$ cfu/g of a bacterial and a fungal composite. The microbes inoculated products were preserved with 0.8%, 1.3%, 2.0% and 3.0% of the total composition of example 6. The cream products were evaluated several times for microbial counts at different days intervals after the first, the third and the fifth inoculation. The cream products were free of microbes 5 days after the first (weak) inoculation and 5 days after the fifth inoculation (strong). The unpreserved (control) cream product was still heavily contaminated at the end of the 10 weeks of observation.

While this invention has been described in detail with reference to certain preferred embodiments, examples and explanations set forth herein are provided for illustrative purposes only, it should be appreciated that the present invention is not limited to those precise embodiments, examples and explanations. Rather, in view of the present disclosure, various modifications and variations would present themselves to those skilled in the art without departing from the scope and spirit of this application and scope of the appended claims.

We claim:

1. An eco-friendly, non-aqueous and stable antimicrobial solution composition comprising:
   a. about 0.1 to 20.0 wt % of a Tropolone; and
   b. about 80.0 to 99.9 wt % of (i) 1,3-propanediol, a bio-derived solvent and/or (ii) sorbitan caprylate, a bio-derived solvent.

2. The antimicrobial composition according to claim 1, wherein said (i) 1,3-propanediol and (ii) sorbitan caprylate are present in the ratio of 1:10 to 10:1.

3. The antimicrobial composition according to claim 1, wherein said (i) 1,3-propanediol and (ii) sorbitan caprylate are present in the ratio of 1:1, 1:3 or 3:1.

4. The antimicrobial composition according to claim 1, wherein the composition is stable for at least two years at room temperature or stable for at least 5 freeze/thaw cycles when the temperature is cycled from 50° C. to −24° C. in every 24 hours or stable for at least 4 weeks at about 50° C.

5. The antimicrobial composition according to claim 1, wherein the composition is capable of inhibiting or killing gram (+) bacteria, gram (−) bacteria, yeast and/or fungi.

6. The antimicrobial composition according claim 1 capable of inhibiting or killing Pseudomonas aeruginosa, Proteus mirabilis, Escherichia coli, Staphylococcus aureus, Burkholderia cepacia, Aspergillus brasiliensis, Penicillium expansum, Trichoderma viride and/or Candida albicans.

7. The antimicrobial composition according to claim 1, wherein said 1,3-propanediol demonstrated synergistic antimicrobial activity against Escherichia coli.

8. The antimicrobial composition according to claim 1, wherein said sorbitan caprylate demonstrated synergistic antimicrobial activity against Burkholderia cepacia, Aspergillus brasiliensis and Trichoderma viride.

9. The antimicrobial composition according to claim 1 employed in the field of cosmetic, toiletry, personal care, household, cleaning, disinfecting, food, beverages, enzyme formulations, feminine care products, foot care products, pet care products, food ingredients, paints, coatings, metal working fluids, nutrients for plants, construction and/or laundry products.

10. The antimicrobial composition according to claim 1 employed in the field of personal care compositions.

11. The antimicrobial composition according to claim 1 employed in the field of shampoo, hair conditioners, skin care lotions, bar soaps, baby bath washes, moisturizers, conditioners, in-shower body moisturizers, body washes, shower gels, hand soaps, wet wipes, hand sanitizers, medicinal creams, cosmetic products, laundry formulations and/or oral care products.

12. The antimicrobial composition according to claim 10 wherein said personal care composition is produced in a form selected from stick, roll-on, spray, pump-spray, aerosol, soap bar, powder, solution, gel, cream, wet wipes, balm and lotion.

13. A process for preparing an eco-friendly, non-aqueous and stable antimicrobial solution composition comprising: preparing a mixture of (a) about 0.1 to 20.0 wt % of a Tropolone; and (b) about 80.0 to 99.9 wt % of 1,3-propanediol, a bio-derived solvent and/or sorbitan caprylate, a bio-derived solvent in ambient/room temperature to yield a homogenous non-aqueous antimicrobial solution.

14. A method for inhibiting or killing microbial growth comprising mixing an effective amount of antimicrobial composition of claim 1 with an appropriate product selected from the group consisting of cosmetic, toiletry, personal care, household, cleaning, disinfecting, food, beverages, enzyme formulations, feminine care products, foot care products, pet care products, food ingredients, paints, coatings, metal working fluids, construction, nutrients for plants and/or laundry products.

15. The method of claim 14 wherein the effective amount of preservative composition is in the range of from about 0.001 wt % to about 25 wt % of the total composition.

16. The method of claim 14 wherein the effective amount of preservative composition is in the range of from about 0.001 wt % to about 5 wt % of the total composition.

17. An eco-friendly, non-aqueous and stable antimicrobial solution composition comprising:
   a. about 0.1 to 20.0 wt % of a Tropolone; and
   b. about 49.95 to 40.0 wt % of (i) 1,3-propanediol, a bio-derived solvent; and about 49.95 to 40.0 wt % of (ii) sorbitan caprylate, a bio-derived solvent.

18. An eco-friendly, non-aqueous and stable antimicrobial solution composition comprising:
   a. about 2.0 wt % of a Tropolone; and
   b. about 49.0 wt % of (i) 1,3-propanediol, a bio-derived solvent; and about 49.0 wt % of (ii) sorbitan caprylate, a bio-derived solvent.

* * * * *